United States Patent [19]

Bonhard et al.

[11] Patent Number: 4,777,244

[45] Date of Patent: Oct. 11, 1988

[54] CROSSLINKED HEMOGLOBIN OF EXTENDED SHELF LIFE AND HIGH OXYGEN TRANSPORT CAPACITY AND PROCESS OF PREPARING SAME

[75] Inventors: Klaus Bonhard, Hanau; Norbert Kothe, Kronberg/Ts., both of Fed. Rep. of Germany

[73] Assignee: Biotest-Serum-Institut GmbH, Frankfurt, Fed. Rep. of Germany

[21] Appl. No.: 47,819

[22] Filed: May 8, 1987

Related U.S. Application Data

[63] Continuation of Ser. No. 439,473, Nov. 5, 1982, abandoned.

[30] Foreign Application Priority Data

Nov. 11, 1981 [DE] Fed. Rep. of Germany ....... 3144705

[51] Int. Cl.$^4$ .......................... C07K 3/08; C07K 15/22
[52] U.S. Cl. .................................. 530/385; 530/402; 530/408; 530/409; 530/410; 424/101
[58] Field of Search ............... 530/385, 402, 408–410; 424/101

[56] References Cited

U.S. PATENT DOCUMENTS 4,061,736 12/1977 Morris et al. ...................... 530/385
4,136,093 1/1979 Bonhard et al. ................... 530/385

OTHER PUBLICATIONS

Characterization of a Modified, Stroma-Free ..., N. Kothe et al. Gyn. & Obs., Dec. 1985, vol. 161, pp. 563–569.
Abstract 428 Methemoglobin Accumulation in Minnesota Hemoglobin, C. Drayton et al., (1982).

*Primary Examiner*—J. R. Brown
*Assistant Examiner*—Jacqueline M. Stone
*Attorney, Agent, or Firm*—Sprung Horn Kramer & Woods

[57] ABSTRACT

Crosslinked hemoglobin preparations of extended shelf life and high oxygen transport capacity can be made by reducing a hemoglobin solution with an oxygen consuming reducing agent down to an oxygen partial pressure of 0 mbar, then adding an effector, crosslinking with a dialdehyde, reducing with a carbonyl-group-specific reducing agent, circulating through an ultrafilter, and stabilizing the product by adding a reducing agent thereto.

6 Claims, 7 Drawing Sheets

Fig. 4a — immediately after preparation

Fig. 4b — 10 weeks after preparation

CROSSLINKED HEMOGLOBIN OF EXTENDED SHELF LIFE AND HIGH OXYGEN TRANSPORT CAPACITY AND PROCESS OF PREPARING SAME

This is a continuation of application Ser. No. 439,473, filed Nov. 5, 1982, now abandoned.

BACKGROUND OF THE INVENTION

The invention relates to a method of preparing a crosslinked hemoglobin preparation of extended shelf life and high oxygen transport capacity, in which a stroma-free hemoglobin solution is treated with an effector and crosslinked with dialdehydes having carbon chains of 3 to 8 carbon atoms, and it relates to the hemoglobin preparation made by this method.

Efforts to use hemoglobin solutions as "blood replacement" have been made since the first half of this century. Developments began with the attempt to administer erythrocyte hemolyzates by infusion. It was found very soon, however, that the stroma components contained in these preparations had a toxic effect on the kidneys, and also affected the chemistry of coagulation. Efforts were then directed to producing stroma-free hemoglobin solutions. There were two different approaches to this. Rabiner et al. were the first to prepare a stroma-free solution in 1967 by centrifugation and ultrafiltration (Rabiner S. F. et al., J. Exp. Med., 126 1127 (1967). This method was improved by K. Bonhard (German Pat. No. 2,248,475). In recent times a crystallized, stroma-free hemoglobin was reported (De Venuto F. et al., J. Lab. Clin. Med. 89, 509 (1977). These stroma-free hemoglobin solutions, however, are not suitable for use as "blood substitute" since they have a number of decided disadvantages.

The intraerythrocytic pH is lower than that of plasma (approx. 7.2 as against 7.4). This difference in acidity causes a leftward shift of the oxygen binding curve, that is, an increase in the oxygen affinity, further intensified by withdrawal of the effector, 2,3-diphosphoglycerate (DPG), which regulates the release of oxygen in the erythrocyte. Hemoglobin solutions prepared by the described method have a half-saturation pressure ($p_{50}$) of only about 16 mbar. It is possible to increase the $p_{50}$ to 31 mbar in vitro by the addition of 2,3-DPG, but, in vivo, due to the weak binding of the DPG to the hemoglobin, the effector is very rapidly excreted by the kidneys. This disadvantage was eliminated by the use of a more strongly bound effector. In German Offenlegungsschrift No. 2,617,822 there is described a method using pyridoxal phosphate which leads to a hemoglobin preparation of greater oxygen yield. Although the problem of low oxygen yield has been solved, there remains a decided disadvantage in the solutions described, namely that the intravascular half life of these solutions amounts to only about 100 minutes. The hemoglobin dissolved in the plasma, due to its structure and its magnitude (molecular weight 64500 D), is rapidly eliminated by the kidneys and, if it is infused in the large amounts necessary for blood replacement, it temporarily impairs renal function.

To extend the intravascular half life a variety of methods have been used, all of them aimed at increasing the molecular weight of the hemoglobin. An attempt was made to link hemoglobin with other macromolecular polymers such as dextran (Chang, J. E., et al, Can. J. Biochem., 55, 398 (1977), hydroxyethyl starch (DE OS No. 2,616,086), gelatine (DE AS No. 2,449,885), albumin (DE AS No. 2,449,885) and polyethylene glycol (DE OS No. 3,026,398). Also, a great variety of crosslinking agents have been used for the purpose of joining the hemoglobin molecules together (DE AS No. 2,449,885, U.S. Pat. Nos. 4,001,200, 4,001,401).

All of these crosslinked preparations do have an extended intravascular half life, but they suffer from a number of other disadvantages.

Binding the hemoglobin molecules to one another or to other macromolecules by bivalent reagents does not result in products of uniform molecular weight, but rather in disperse systems of great molecular weight distribution, ranging from the four-chain basic molecule through oligomers thereof to highly polymerized molecules. What influence such a broad molecular weight distribution has on the tolerability of these solutions is not yet fully known, but it is argued that histological alterations to the kidneys and livers of experimental animals are to be attributed to polymeric and monomeric components, respectively.

Chemical modifications of the hemoglobin molecule often affect the oxygen binding curve. In most cases the affinity for oxygen is increased, so that less oxygen is yielded to tissue under physiological conditions. In other cases, the chemically altered hemoglobin receives a low charge of oxygen under the oxygen partial pressure in the lungs, so that adequate oxygen transport is not assured. The binding of effectors such as pyridoxal phosphate prior to crosslinking militates against an increase of oxygen affinity, but it has not been possible repeatably to obtain a $p_{50}$ above 27 mbar at the plasmatic pH of 7.4.

The crosslinking at the same time greatly reduces the shelf life of hemoglobin solutions. The factor that limits shelf life is the formation of methemoglobin, which does not transport oxygen, and gradually renders the solution ineffectual.

It was the object of the invention to prepare a crosslinked hemoglobin preparation, that is, one of extended intravascular half life, which
(a) will have a narrow molecular weight distribution, i.e., will be free of highly polymerized hemoglobin and low in noncrosslinked hemoglobin,
(b) will retain this stable molecular weight distribution and, despite the crosslinking,
(c) will have a high oxygen transporting ability and
(d) a good stability (shelf life).

SUMMARY OF THE INVENTION

This object is achieved in accordance with the invention by treating a stroma-free, concentrated hemoglobin solution with so much of an oxygen consuming reducing agent that the oxygen partial pressure is lowered to 0 mbar, treating the deoxygenated product thus obtained in a known manner with a physiologically tolerable effector, and, then, with a dialdehyde at a pH between 6 and 8, reducing the crosslinked product with 5 to 20 times the amount of a carbonyl-group-specific reducing agent, diluting the solution with water and treating it, if desired, with active carbon, and circulating it with a pump through an ultrafilter filter until the content of noncrosslinked hemoglobin amounts to no more than 15%, the crosslinking being performed before or during the ultrafiltration, and stabilizing the product by the addition of a reducing agent.

The hemoglobin preparations made according to the invention have none of the disadvantages described above.

The desired properties (a) to (d) specified above are achieved substantially by the following steps of the overall process:
(a) by ultrafiltration;
(b) by reduction with a carbonyl-group-specific reducing agent,
(c) by complete chemical deoxygenation with an oxygen-consuming reducing agent, and
(d) by the addition of reducing substances to the crosslinked, ultrafiltered hemoglobin preparation.

The crosslinking is performed with dialdehydes containing carbon chains of 3 to 8 carbon atoms, such as those described, for example, in U.S. Pat. No. 4,336,248.

To lower the oxygen affinity, the crosslinking is preceded by treatment with a physiologically tolerable effector, for example with pyridoxal phosphate, as described in U.S. Pat. No. 4,136,093, or with inositol hexaphosphate, as described in DE OS No. 2,740,053.

Solutions prepared by these above-described methods have an elevated oxygen affinity ($p_{50}$ approximately 20 mbar).

In one embodiment of the crosslinking process described in U.S. Pat. No. 4,336,248, the hemoglobin solutions are converted to the deoxy form prior to the crosslinkin9, but the deoxygenation is performed by evacuation and flooding with nitrogen. However, when relatively great amounts are used the deoxygenation is not complete. In an attempt to deoxygenate two liters of 18% hemoglobin solution in a five liter vessel by this method, even after 40 repetitions the oxygen partial pressure dropped only to 33 mbar. It can be seen from the oxygen binding curve that the hemoglobin is still 75% saturated at this oxygen partial pressure.

Surprisingly it was found that a crosslinked, reduced and ultrafiltered hemoglobin preparation treated with an effector such as pyridoxal phosphate, can be prepared with a $p_{50}$ of 33–38 mbar at pH 7.4 if the hemoglobin solution is converted to the deoxy form completely, that is, chemically, prior to the crosslinking.

In accordance with the invention, all of the oxygen is removed from the solution by an oxygen-consuming reducing agent, such as ascorbic acid, reduced glutathion or reduced methylene blue, or preferably neutralized ascorbic acid. The effectiveness of this method is to be seen in Table 1.

TABLE 1

| Moles of ascorbic acid neutralized with NaOH moles of hemoglobin | $pO_2$ (mbar) |
| --- | --- |
| 0 | 263 |
| 0.5 | 71 |
| 1 | 48 |
| 2 | 31 |
| 3 | 17 |
| 4 | 0 |

The invention will be further described with reference to the accompanying, drawings wherein.

Figure 3:
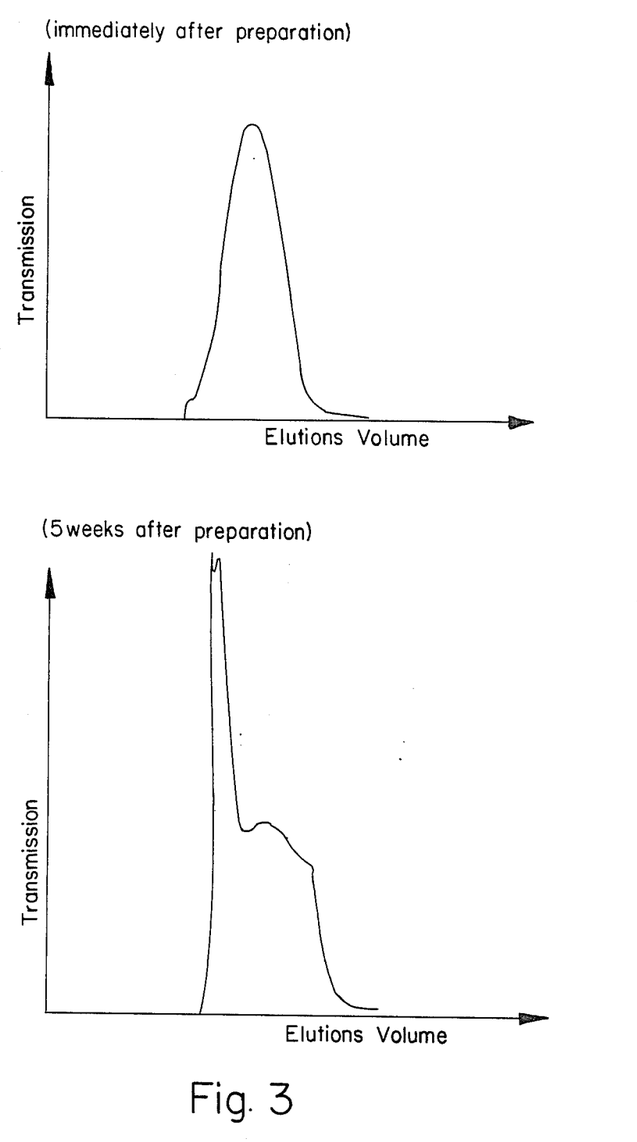
FIG. 3 is a pair of graphs showing the change in the relationship of eluate volume to transmission of a prior art product upon standing; pair of graphs showing the stability in FIG. 4 is a pair of graphs showing the stability in the relationship of eluate volume to transmission of a product reduced in accordance with the invention.

The crosslinked hemoglobin solutions of the prior art, described above, have the disadvantage that the stability of the molecular weight distribution is limited. While they are in storage a shift toward greater molecular weights takes place (FIG. 3). The reaction of aldehydes with amino groups to azomethines takes place very rapidly; that is, it is kinetically controlled. The azomethine bond, however, is easy to cleave hydrolytically, so that thermodynamically more stable bonds can form during storage by rearrangement of the azomethine bond. To prevent this, the azomethine bond is stabilized by reduction with a carbonyl-group-specific reducing agent, such as $NaBH_4$, $KBH_4$ or $NaCNBH_3$, and catalytic hydrogenation.

Figure 4A:
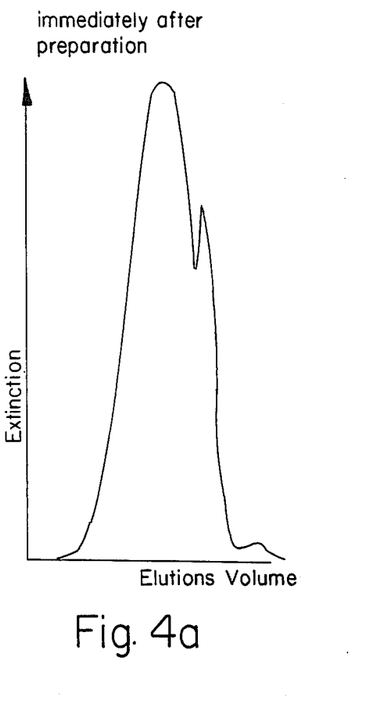
Figure 4B:
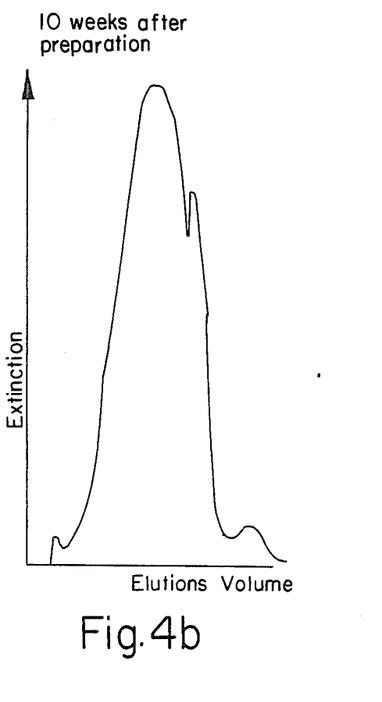

In FIG. 4 there is represented an example of reduction with $NaBH_4$. The $BO_3$ that forms in the reaction is removed in the ultrafiltration.

Another advantage is offered by the reduction process if pyridoxal phosphate is used as the effector molecule. The pyridoxal phosphate is also bound to the hemoglobin molecule by an azomethine bond. By means of the reduction, therefore, not only is the crosslinking stabilized, but also the effector is fixed to its specific binding point.

The ultrafiltration apparatus used for the achievement of a crosslinked hemoglobin derivative that is free of polymerized hemoglobin and very low in noncrosslinked hemoglobin consists preferably of hollow fiber cartridges. However, flat membrane filters can also be used.

The ultrafiltration can be performed by means of the two systems described hereinbelow.

Figure 1:
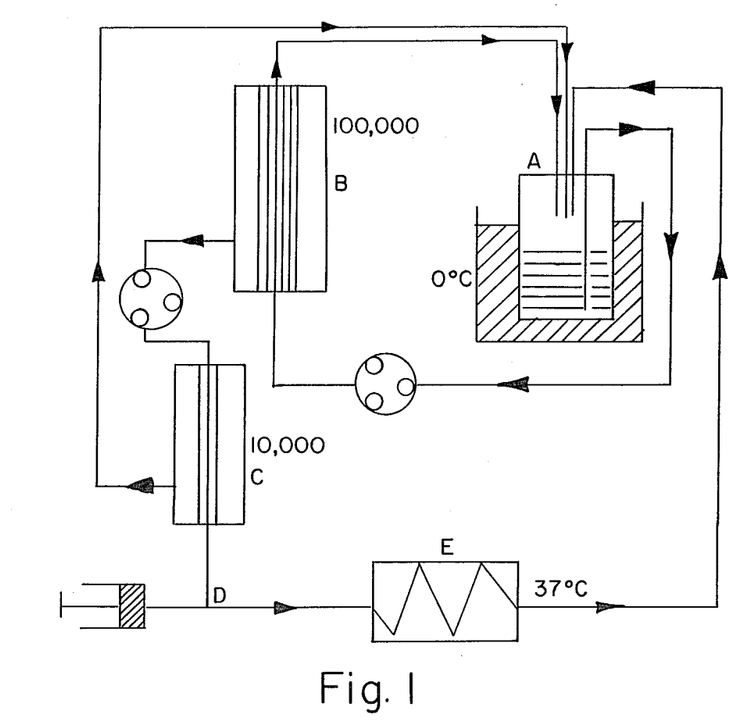
FIG. 1 is a schematic flow sheet of one process in accordance with the present invention.

System 1 (FIG. 1)

A deoxygenated, noncrosslinked hemoglobin solution to which effector has been added is placed in the refrigerated supply vessel A and circulated by pumping through the hollow fiber unit B which has a permeability of molecular weight 100,000. The ultrafiltrate is initially concentrated by means of a second hollow fiber unit C having a permeability of 10,000. It is mixed at D with the crosslinking agent, heated in the reaction bath E to 37° C., and returned to the supply vessel A. The crosslinked molecules can no longer pass through the membrane of the ultrafiltration unit B. This arrangement assures that any crosslinked hemoglobin will be unable to come a second time in contact with crosslinking agent; in other words, the formation of polymers is prevented. The remainder of hemoglobin that is still not crosslinked can be removed by ultrafiltration after the reaction has ended.

Figure 2:
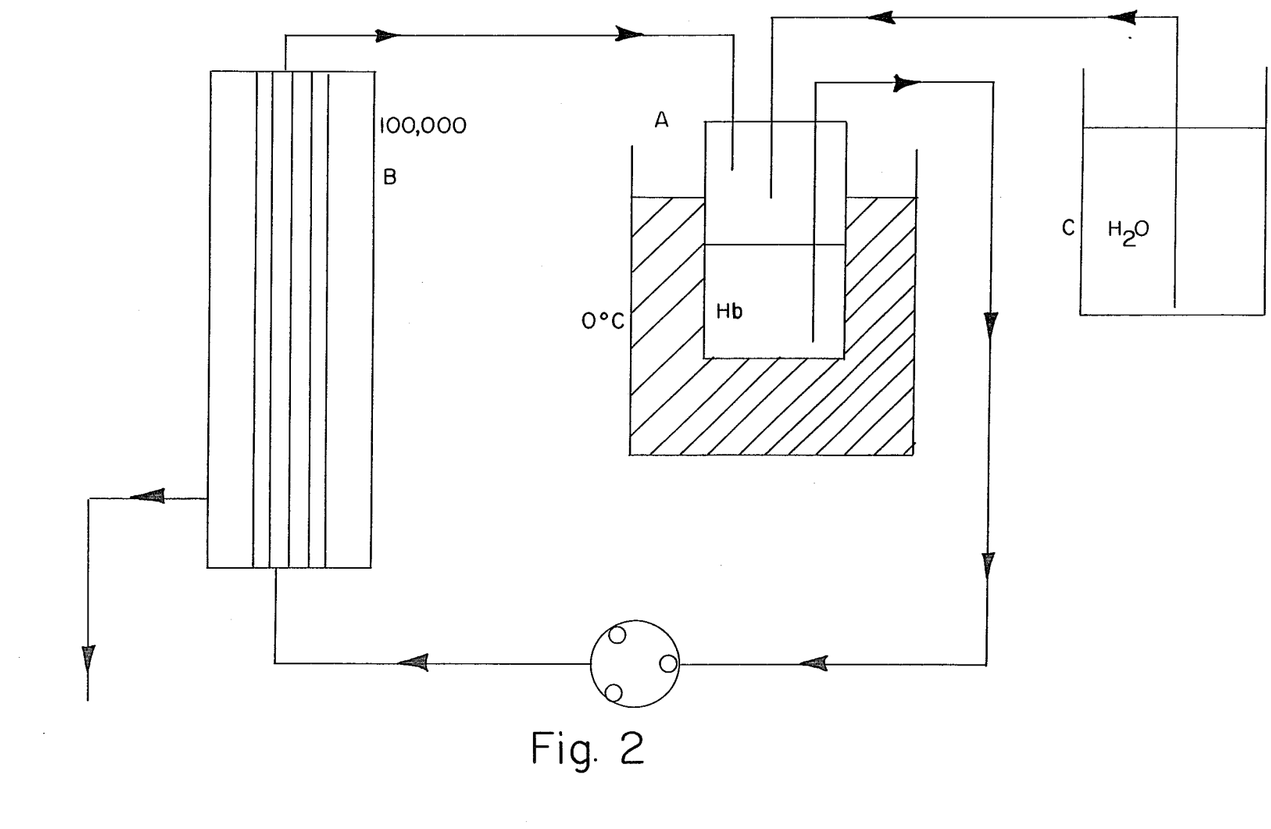
FIG. 2 is a schematic flow sheet of another process in accordance with the invention.

System 2 (FIG. 2)

The second possibility for arriving at a more uniformly crosslinked product is based on the following consideration. In the crosslinking reaction intermolecular and intramolecular crosslinking compete. By increasing the hemoglobin concentration the reaction can be shifted in favor of intermolecular crosslinking. Now, if the amount of the crosslinking agent is selected such that no polymeric product forms, then, in addition to a certain amount of noncrosslinked hemoglobin, only oligomers are obtained. The noncrosslinked hemoglobin molecules are partially separated in subsequent ultrafiltration on a membrane with a cutoff at molecular weight 100,000. The crosslinking reaction takes place in reaction vessel A. After the end of the reaction the solution is circulated by pumping through the ultrafiltration unit B, in which noncrosslinked hemoglobin passes through the membrane. The loss of volume in the circuit due to the outflow of the ultrafiltrate is made up with water from the supply vessel C.

Crosslinked oligomeric hemoglobin solutions (Mn approximately 200,000 D) prepared by these methods contain no polymeric hemoglobins and less than 15% of noncrosslinked hemoglobin.

While in System 1 the process sets out from noncrosslinked hemoglobin solutions and the crosslinking takes place during recirculation throuoh the ultrafilter, which is controlled such that no polymeric products are formed, in System 2 crosslinked products having an already-controlled crosslinking are used.

After the reaction with the reagent specific for carbonyl groups, the mixture is diluted with water to collapse the foam on the very frothy solution.

For the reduction of lipophilic substance and improvement of the filtration, the dilute solution can be treated with active carbon if desired.

The overall process of the invention takes place, if System 2 is used, as follows:

The initial 15 to 30-percent hemoglobin solution is treated, depending on the oxygen partial pressure, with so much of an oxygen consuming reducing agent, such as ascorbic acid neutralized with caustic soda, that the oxygen partial pressure is reduced to 0 mbar. In the case of a hemoglobin saturated with oxygen gas, this will be four moles of ascorbic acid per mole of hemoglobin. The solution cooled to 0° to 10° C. is treated with 2 to 5 times, preferably with 3.35 times the number of moles of an effector such as pyridoxal phosphate or inositol hexaphosphate. Then the crosslinking is performed with the dialdehyde at pH 6 to 8, preferably 7.0, in a preferably 10% aqueous solution, the amount being proportioned such that no polymeric hemoglobin is formed.

The reduction that follows is performed with 5 to 20 times, preferably 13.8 times, the molar amount of the carbonyl-group-specific reducing agent, such as $NaBH_4$, measured on the starting hemoglobin.

Then an ultrafiltration is performed through a filter of a permeability up to a molecular weight of 100,000 D until the amount of noncrosslinked hemoglobin is between 5 and 15% of the total hemoglobin in the unfiltrate.

The shelf life of crosslinked hemoglobin solutions is limited by the formation of methemoglobin. In accordance with the invention, these hemoglobin preparations are stabilized against autooxidation by the addition of reducing substances such as ascorbic acid, reduced glutathion or reduced methylene blue. After a storage period of one year, the methemoglobin content is still less than 10% of the total hemoglobin, and it is immaterial which effector is used. Preferably, ascorbic acid is used for stabilization in a fourfold molar excess with respect to the hemoglobin.

Figure 5:
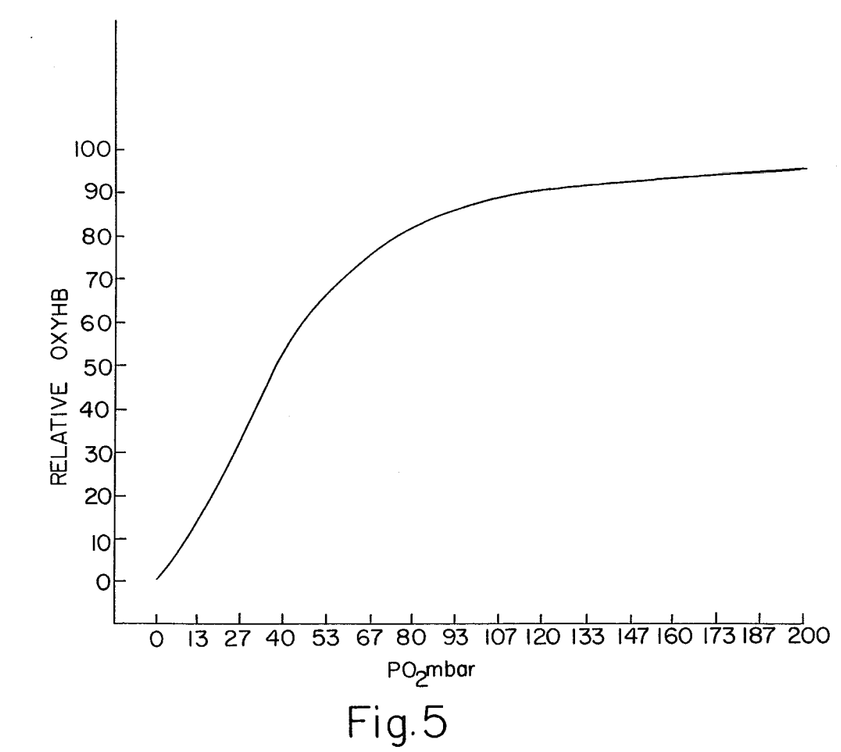
FIG. 5 is a graph showing the relationship of oxygen binding to $pO_2$ using pyridoxal phosphate.

The oxygen binding curve of the crosslinked hemoglobin solution prepared in accordance with the invention using pyridoxal phosphate is represented in FIG. 5. The $p_{50}$ amounts to 36 mbar. Surprisingly, the curve is sigmoidal, similar to that of the native hemoglobin. Such a curve has never before been found in crosslinked hemoglobins.

Figure 6:
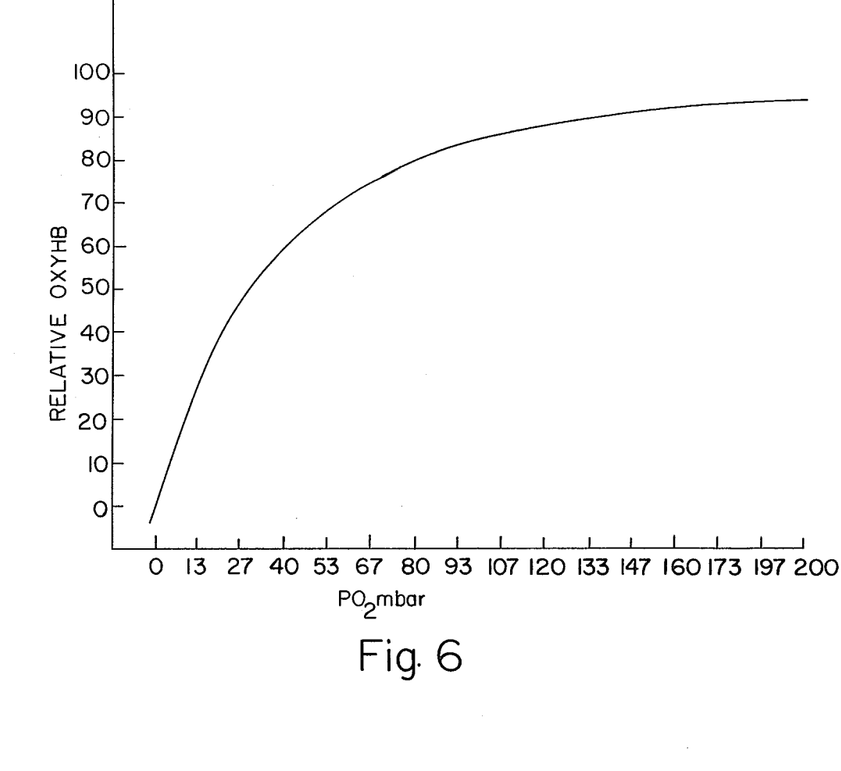
FIG. 6 is a graph showing the relationship of oxygen binding to $pO_2$ using inositol phosphate.

The oxygen binding curve obtained with the use of inositol hexaphosphate is represented in FIG. 6.

Both the effectiveness and the tolerability of the hemoglobin solutions prepared by the method of the invention have been proven in animal experiments on rabbits and rats.

The preparations made by the method of the invention were free of pyrogens.

The following examples will serve for the further elucidation of the invention.

EXAMPLES

A hemoglobin solution prepared in accordance with Example 1 of DE PS No. 2,248,475 was brought to a concentration of 19.6% by ultrafiltration with a hollow fiber cartridge having a permeability of up to a molecular weight of 100,000 D. To this solution a four-fold molar excess of neutralized ascorbic acid was added, the mixture was sterile-filtered, and let stand for at least 24 hours. 842 ml of this deoxygenated 19% hemoglobin solution was placed in the reactor, chilled, and treated with 4.3 g of $NaH_2PO_3$ as well as 3 g of $Na_2HPO_4$ dissolved in a little water.

Then, with stirring, 2.2 g of pyridoxal phosphate was added. The pH dropped to 6.6. The reaction time was one hour. After this time, with vigorous stirring, 13.9 ml of 10% aqueous glutaric dialdehyde solution was added and the mixture was stirred again for one hour. For the reduction, there were added 1.34 g of $NaBH_4$ which had been dissolved shortly beforehand in a little water. After 30 minutes of reaction time, the greatly frothing solution was diluted with 6 liters of water, whereupon the foam largely collapsed, and this solution was filtered through a sterile filter after one hour of treatment with 10 grams per liter of active carbon. For the ultrafiltration through the hollow fiber cartridge of a permeability of up to 100,000 D molecular weight, first the ultrafiltration system was filled, and then 1.1 liters of the dilute solution were placed in a closed vessel. This amount was constantly recirculated with a pump. The loss of volume caused by the ultrafiltrate was constantly replaced with the dilute hemoglobin solution. In this manner the solution was again concentrated. As soon as the hemoglobin solution had been consumed in replacement of the volume loss, the ultrafiltration was continued with 9 liters of distilled water and then concentrated to about 10 to 11%. For the adjustment of the colloidal osmotic pressure and hemoglobin concentration, 115 ml of 20% human albumin was added. Prior to the final sterile filtration, the following constituents were also added: 3.32 g NaCl, 14.5 g glucose, 1.66 g $NaHCO_3$, 0.26 g KCl, and 0.16 g $MgSO_4$, and, for stabilization, 0.61 g of neutralized ascorbic acid.

Figure 7A:
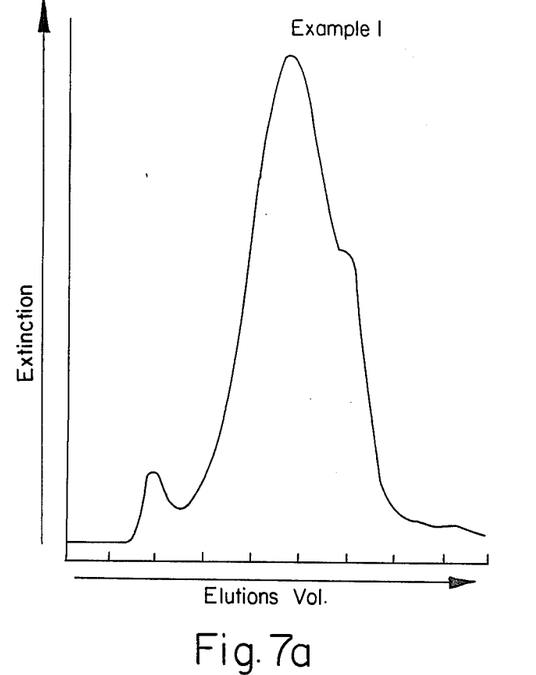
FIG. 7a is a plot of eluate volume vs. extinction of instant Example 1.

Yield: 660 ml
Hemoglobin content: 8.5%
Methemoglobin: 5.1 rel. %
Colloidal osmotic pressure 36.8 mbar
$p_{50}$ = 38.6 mbar
Relative viscosity 2.6
Molecular weight distribution, see FIG. 7a.
(Gel chromatographic profile on sepharose 6B)

EXAMPLE 2

The procedure was the same as in Example 1. Instead of pyridoxal phosphate, 2.59 g of inositol hexaphosphate, dissolved in water and adjusted to pH 7.6, was added as effector.

Figure 7B:
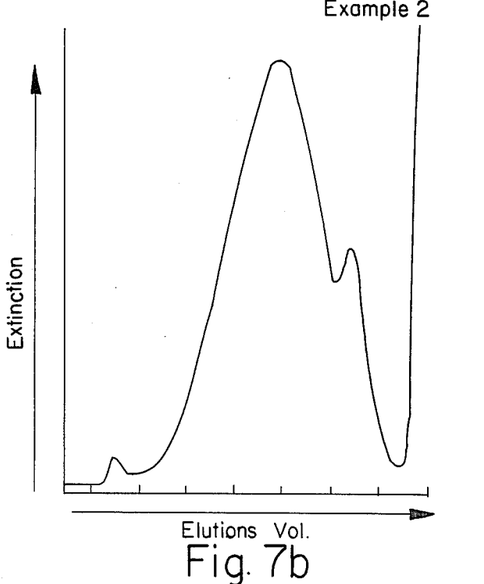
FIG. 7b is a plot of eluate volume vs. extinction for the product of instant Example 2.

Yield: 925 ml
Hemoglobin content: 8.9%
Methemoglobin: 2.6 rel. %
$p_{50}$: 27 mbar
For molecular weight distribution, see FIG. 7b.
(Gel chromatographic profile on Sepharose 6B)

It will be understood that the specification and examples are illustrative but not limitative of the present invention and that other embodiments within the spirit and scope of the invention will suggest themselves to those skilled in the art.

We claim:

1. In the preparation of a crosslinked hemoglobin of extended shelf life and high oxygen transport capacity wherein a stroma-free hemoglobin solution is treated with an effector and crosslinked with a dialdehyde having carbon chains of 3 to 8 carbon atoms, the improvement which comprises contacting a stroma-free, concentrated hemoglobin solution with so much of an ox/gen-consuming reducing agent that the $O_2$ partial pressure diminishes to substantiall 0 mbar, contacting the deoxygenated product thus obtained with a physiologically tolerable effector and then, at a pH between about 6 and 8, with the dialdehyde, reducing the crosslinked product so obtained with about 5 to 20 times the molar amount of a carbonyl-group-specific reducing agent, diluting the solution with water, ultrafiltering and recirculating the solution until the content of uncrosslinked hemoglobin amounts to no more than about 15%, the crosslinking being effected before or during the ultra-filtration, and adding a reducing agent thereby to stabilize the solution.

2. The process according to claim 1, wherein the effector comprises pyridoxal phosphate or inositol hexaphosphate.

3. The process according to claim 1, wherein the oxygen-consuming reducing agent is ascorbic acid, reduced glutathion, reduced methylene blue or neutralized ascorbic acid.

4. The process according to claim 3, wherein the oxygen consuming reducing agent is neutralized ascorbic acid.

5. The process according to claim 1, wherein the carbonyl-group-specific reducing agent comprises $NaBH_4$.

6. The crosslinked hemoglobin preparation of long shelf life and high oxygen transport capacity produced by the process of claim 1.

* * * * *

UNITED STATES PATENT AND TRADEMARK OFFICE
CERTIFICATE OF CORRECTION

PATENT NO. : 4,777,244
DATED : October 11, 1988
INVENTOR(S) : Klaus Bonhard, et al It is certified that error appears in the above-identified patent and that said Letters Patent is hereby corrected as shown below:

| | |
|---|---|
| Col. 3, lines 25-26 | Correct --crosslinking-- |
| Col. 3, line 67 | After "standing;" delete "pair of graphs showing the stability in" |
| Col. 4, line 8 | After "extinction" insert --for the product-- |
| Col. 7, line 26 | Delete "ox/gen" and substitute --oxygen-- |
| Col. 7, line 27 | Correct substantially-- |

Signed and Sealed this

First Day of August, 1989

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,777,244

DATED : October 11, 1988

INVENTOR(S) : Klaus Bonhard, et al

It is certified that error appears in the above-identified patent and that said Letters Patent is hereby corrected as shown below:

Col. 4, line 2          Delete "transmission" and substitute --extinction--

Col. 4, line 27        Delete "BO$_3$" and substitute --BO$_3^{3-}$--

Signed and Sealed this

Twentieth Day of March, 1990

Attest:

JEFFREY M. SAMUELS

Attesting Officer      Acting Commissioner of Patents and Trademarks